United States Patent [19]

Anton et al.

[11] Patent Number: 5,439,813

[45] Date of Patent: * Aug. 8, 1995

[54] PRODUCTION OF GLYOXYLIC ACID WITH GLYCOLATE OXIDASE AND CATALASE IMMOBILIZED ON OXIRANE ACRYLIC BEADS

[75] Inventors: David L. Anton; Robert DiCosimo; John E. Gavagan, all of Wilmington, Del.

[73] Assignee: E. I. Du Pont de Nemours and Company, Wilmington, Del.

[*] Notice: The portion of the term of this patent subsequent to Jun. 15, 2010 has been disclaimed.

[21] Appl. No.: 253,812

[22] Filed: Jun. 3, 1994

Related U.S. Application Data

[63] Continuation of Ser. No. 755,926, Sep. 6, 1991, abandoned.

[51] Int. Cl.$^6$ .......................... C12P 7/40; C12N 9/04; C12N 9/08
[52] U.S. Cl. ........................... 435/136; 435/190; 435/192
[58] Field of Search ............... 435/140, 190, 136, 192

[56] References Cited

U.S. PATENT DOCUMENTS

| | | | |
|---|---|---|---|
| 3,281,460 | 10/1966 | Gandon | 260/530 |
| 4,094,928 | 6/1978 | Gaertner et al. | 260/944 |
| 4,146,731 | 3/1979 | Ogahara et al. | 562/531 |
| 4,233,452 | 11/1980 | Williams et al. | 549/79 |
| 4,235,684 | 11/1980 | Harada et al. | 204/79 |
| 4,455,371 | 6/1984 | Richardson et al. | 435/25 |
| 4,460,686 | 7/1984 | Hartmeier | 435/137 |
| 4,670,191 | 6/1987 | Kleiner et al. | 260/502.5 F |
| 4,871,669 | 10/1989 | Murray et al. | 435/147 |
| 5,126,247 | 6/1992 | Palmer et al. | 435/25 |
| 5,219,745 | 6/1993 | Anton et al. | 435/136 |
| 5,221,621 | 6/1993 | Anton et al. | 435/136 |
| 5,851,159 | 7/1989 | Fields et al. | 562/17 |

FOREIGN PATENT DOCUMENTS 2186648 12/1985 European Pat. Off. .
0413672 2/1991 European Pat. Off. .

OTHER PUBLICATIONS

Tolbert et al., "J. Biol. Chem." vol. 181 pp. 905–914 (1949).

Richarson et al., "J. Biol. Chem." vol. 236 pp. 1280–1284 (1961).

Clagette et al., "J. Biol. Chem.", vol. 178, pp. 977–987 (1961).

Zelitch et al., "J. Biol. Chem." vol. 201 pp. 707–718 (1953).

(List continued on next page.)

Primary Examiner—David M. Naff
Assistant Examiner—Mike Meller

[57] ABSTRACT

A process for the production of glyoxylic acid by reacting glycolic acid with oxygen in an aqueous solution in the presence of an amine buffer capable of forming a chemical adduct with glyoxylic acid, and glycolate oxidase and catalase immobilized or co-immobilized on an insoluble support is disclosed. The reaction is carried out at a pH of 7 to 10, preferably 8 to 9.5, an initial concentration of glycolic acid of 200 to 2500 mM, a concentration of amine wherein the initial mole ratio of amine to glycolic acid is within the range of 1.0 to 3.0, a concentration of immobilized catalase of 50 to 100,00 IU/mL, preferably 350 to 14,000 IU/mL, an oxygen pressure of up to 50 atmospheres, preferably 15 atmospheres, an immobilized glycolate oxidase concentration of about 0.01 to 10 IU/mL, preferably about 0.1 to 4 IU/mL, and a temperature of 0° to 40° C. preferably 5° to 15° C. Preferred insoluble immobilization supports are Eupergit C-250L and Eupergit C (Oxirane acrylic beads).

15 Claims, No Drawings

OTHER PUBLICATIONS

Robinson et al., "J. Biol. Chem.", vol. 237, pp. 2001–2009 (1962).

Frigerio et al., "J. Biol. Chem.," vol. 231 pp. 135–157 (1958).

Zelitch et al., "Methods in Enzymology" vol. 1 pp. 528–532 (1955).

Nishimura et al., "Arch. Biochem. Biophys." vol. 222 pp. 397–402 (1983).

Asker et al., "Biochim Biophys. Acta." vol. 761 pp. 103–108 (1983).

Emes et al., "Int. J. Biochem.", vol. 16 1373–1378 (1984).

Cederlund et al., "Eur. J. Biochem." vol. 172 pp. 523–530 (1988).

Lindquist et al., "J. Biol. Chem." vol. 264, pp. 3624–3628 (1989).

Yagai, "Methods of Biochemical Analysis," vol. 8 pp. 319–355 (1962).

Volokito et al., "J. Biol. Chem." vol. 262, 15825 (1987).

Macheroux et al., "Biochemistry", vol. 30 pp. 4612–4619 (1991).

Seah et al., "J. Biol. Chem." vol. 218 No. 8 p. 2880 (1973).

Pollack, et al., "J. Am. Chem. Soc.", vol. 102 pp. 6324–6336 (1980).

Kerr, M. N., Graves, D., "Phytochemistry," vol. 14 pp. 359–362 (1975).

PRODUCTION OF GLYOXYLIC ACID WITH GLYCOLATE OXIDASE AND CATALASE IMMOBILIZED ON OXIRANE ACRYLIC BEADS

This is a continuation of application Ser. No. 07/755,926 filed Sep. 6, 1991, now abandoned.

BACKGROUND OF THE INVENTION

1. Field of the Invention

This invention relates to an improved process for the production of glyoxylic acid by the enzyme catalyzed oxidation of glycolic acid. More specifically, the present invention relates to the use of glycolate oxidase and catalase immobilized on an insoluble support as catalyst.

2. Description of the Related Art

Glycolate oxidase, an enzyme commonly found in leafy green plants and mammalian cells, catalyzes the oxidation of glycolic acid to glyoxylic acid, with the concomitant production of hydrogen peroxide. N. E. Tolbert et al., *J. Biol. Chem.*, Vol. 181, 905–914 (1949) first reported an enzyme, extracted from tobacco leaves, which catalyzed the oxidation of glycolic acid to formic acid and $CO_2$ via the intermediate formation of glyoxylic acid. The addition of certain compounds, such as ethylenediamine, limited the further oxidation of the intermediate glyoxylic acid. The oxidations were carried out at a pH of about 8, typically using glycolic acid concentrations of about 3–40 mM (millimolar). The optimum pH for the glycolate oxidation was reported to be 8.9. Oxalic acid (100 mM) was reported to inhibit the catalytic action of the glycolate oxidase. Similarly, K. E. Richardson and N. E. Tolbert, *J. Biol. Chem.*, Vol. 236, 1280–1284 (1961) showed that buffers containing tris(hydroxymethyl)aminomethane inhibited the formation of oxalic acid in the glycolate oxidase catalyzed oxidation of glycolic acid. C. O. Clagett, N. E. Tolbert and R. H. Burris, *J. Biol. Chem.*, Vol. 178, 977–987 (1949) reported that the optimum pH for the glycolate oxidase-catalyzed oxidation of glycolic acid with oxygen was about 7.8–8.6, and the optimum temperature was 35°–40° C.

I. Zelitch and S. Ochoa, *J. Biol. Chem.*, Vol. 201, 707–718 (1953), and J. C. Robinson et al., *J. Biol. Chem.*, Vol. 237, 2001–2009 (1962), reported that the formation of formic acid and $CO_2$ in the spinach glycolate oxidase-catalyzed oxidation of glycolic acid resulted from the nonenzymatic reaction of $H_2O_2$ with glyoxylic acid. They observed that addition of catalase, an enzyme that catalyzes the decomposition of $H_2O_2$, greatly improved the yields of glyoxylic acid by suppressing the formation of formic acid and $CO_2$. The addition of FMN (flavin mononucleotide) was also found to greatly increase the stability of the glycolate oxidase.

N. A. Frigerio and H. A. Harbury, *J. Biol. Chem.*, Vol. 231, 135–157 (1958) have reported on the preparation and properties of glycolic acid oxidase isolated from spinach. The purified enzyme was found to be very unstable in solution; this instability was ascribed to the relatively weak binding of flavin mononucleotide (FMN) to the enzyme active site, and to the dissociation of enzymatically active tetramers and/or octamers of the enzyme to enzymatically-inactive monomers and dimers, which irreversibly aggregate and precipitate. The addition of FMN (flavin mononucleotide) to solutions of the enzyme greatly increased its stability, and high protein concentrations or high ionic strength maintained the enzyme as octamers or tetramers.

There are numerous other references to the oxidation of glycolic acid catalyzed by glycolic acid oxidase, for example:

Isolation of the enzyme (usually includes an assay method):

I. Zelitch in *Methods of Enzymology*. Vol. 1, Academic Press, New York, 1955, p. 528–532, from spinach and tobacco leaves.

M. Nishimura et al., *Arch. Biochem. Biophys.*, Vol. 222, 397–402 (1983), from pumpkin cotyledons.

H. Asker and D. Davies, *Biochim. Biophys. Acta*, Vol. 761, 103–108 (1983), from rat liver.

M. J. Emes and K. H. Erismann, *Int. J. Biochem.*, Vol. 16, 1373–1378 (1984), from Lemna Minor L.

Structure of the enzyme:

E. Cederlund et al., *Eur. J. Biochem.*, Vol. 173, 523–530 (1988).

Y. Lindquist and C. Branden, *J. Biol. Chem.* Vol. 264, 3624–3628, (1989).

SUMMARY OF THE INVENTION

This invention relates to a process for the production of glyoxylic acid (OCHCOOH) where glycolic acid ($HOCH_2COOH$) (200 to about 2500 mM) and oxygen are reacted in an aqueous solution (pH 7 to 10), in the presence of a catalyst consisting of glycolate oxidase ((S)-2-hydroxy-acid oxidase, EC 1.1.3.15) and catalase (EC 1.11.1.6) immobilized on an insoluble support. Under optimum conditions, very high yields of glyoxylic acid are obtained at high conversion of glycolic acid, and the immobilized enzyme catalyst can be recovered and reused.

DESCRIPTION OF THE PREFERRED EMBODIMENTS

This invention describes the preparation and use of an immobilized enzyme catalyst for the manufacture of glyoxylic acid from glycolic acid (hydroxyacetic acid). Although the enzyme-catalyzed reaction of glycolic acid with oxygen has been known for many years, high selectivities (>99%) to glyoxylic acid have not been previously obtained, nor has the oxidation of glycolic acid been performed at concentrations of 0.20M to 2.5M. A previous, commonly assigned, application, U.S. Ser. No. 07/422,011, filed Oct. 16, 1989, "Production of Glyoxylic Acid from Glycolic Acid", described a process for the enzymatic conversion of glycolic acid to glyoxylic acid in the presence of oxygen, an amine buffer, and the soluble enzymes glycolate oxidase and catalase. This process demonstrated the unexpected synergistic effect of using both catalase (to destroy by-product hydrogen peroxide) and an amine buffer capable of forming a chemical adduct with the glyoxylic acid produced (limiting its further oxidation) and is herein incorporated by reference for such purpose. Neither the separate addition of catalase or an amine buffer were found to produce the high selectivity observed when both were present, and the almost quantitative yields of glyoxylic acid obtained were more than expected from a simple additive effect of using catalase or amine buffer alone. The instant invention is viewed as an improvement to the above process in that an immobilized enzyme catalyst is provided for this process.

A previously-reported use of soluble enzymes as catalysts poses several problems: catalyst recovery for reuse is not easily performed, catalyst stability is not as good as can be obtained with immobilized enzyme systems, and soluble enzymes are not stable to the sparging of the reaction mixture with oxygen (required to increase the rate of oxygen dissolution and, thus, reaction rate). A catalyst preparation has now been developed which involves the simultaneous immobilization of the two enzymes; i.e., glycolate oxidase (e.g., from spinach or beet leaves, isolated or obtained from commercial sources) and catalase (e.g., from *Aspergillus niger, Aspergillus nidulans, Saccharomyces cerevisae* (Baker's yeast), or bovine liver, isolated or obtained from commercial sources), on a solid support (e.g. commercially available oxirane acrylic beads). Several advantages are offered by the use of this immobilized enzyme catalyst in the previously described process:

1) the immobilized catalyst is easily recovered from the reaction mixture at the conclusion of the reaction for reuse, whereas the soluble enzyme is only recovered with great difficulty and loss of activity;
2) the immobilized catalyst is more stable than the soluble enzyme, both for the number of catalyst turnovers obtained versus the soluble enzyme, as well as for recovered enzyme activity at the conclusion of a reaction or after prolonged storage in aqueous buffer; and
3) most importantly, the immobilized catalyst is stable to reaction conditions where oxygen is sparged into the reaction mixture to increase the rate of oxygen dissolution and reaction rate, where under similar reaction conditions the soluble glycolate oxidase is rapidly denatured.

No one method of immobilization can be chosen for a particular enzyme with the expectation that the immobilization will be successful. Furthermore, the expectation for successful co-immobilization of more than one enzyme is even less predictable. It is generally agreed by those skilled in the art that a successful immobilization of any one enzyme must be discovered by screening a variety of methods, and an optimal result obtained by trial and error. In the case of glycolate oxidase, there have been no reports of attempts at immobilization. The immobilization of enzymes can be performed using a variety of techniques, including: (1) binding of the enzyme to a carrier or support, via covalent attachment, physical adsorption, electrostatic binding, or affinity binding, (2) crosslinking with bifunctional or multifunctional reagents, (3) entrapment in gel matrices, polymers, emulsions, or some form of membrane, and (4) a combination of any of these methods. Detailed descriptions of many of these methods of enzyme immobilization, and the various factors affecting the choice of a method of immobilization, are collected in the following volumes of Methods in Enzymology, K. Mosbach (ed.), Academic Press, New York: Vol. 44 (1976), Vol. 135 (1987), Vol. 136 (1987), Vol. 137 (1988), and the references therein.

A variety of methods of immobilization of glycolate oxidase were examined, and the optimal results for a number of these procedures are listed in the Examples. Covalent attachment of the protein to oxirane acrylic beads (Eupergit C), cyanogen bromide-activated agarose, and poly(acrylamide-co-N-acryloxysuccinimide) gel crosslinked with triethylenetetramine (PAN-500) produced active immobilized enzyme, as did physical adsorption to the resin XAD-8 and phenyl agarose. Ionic binding to various supports was unsuccessful, as were attempts at crosslinking the protein with glutaraldehyde, dimethyl adipimidate, dimethylsuberimidate, or 1,4-butanediol diglycidyl ether. Of the different forms of active immobilized glycolate oxidase, only the oxirane acrylic bead-enzyme was useful as a catalyst for the oxidation of glycolic acid. The physically-adsorbed enzyme rapidly desorbed from the support in the reaction mixture containing 0.75M glycolic acid and 0.79M ethylenediamine at pH 9.0, while the cyanogen bromide-activated agarose reacted with the ethylene diamine, again releasing the covalently-bound enzyme into the reaction mixture. The specific activity of the enzyme attached to PAN-500 gel was too low to be useful as a practical catalyst in the reaction.

The immobilization of glycolate oxidase on oxirane acrylic beads Eupergit C and Eupergit C-250L (Rohm Pharma) resulted in a catalyst which was stable to the reaction conditions, and had a sufficiently high specific activity (units of enzyme activity/gram of catalyst) to be useful in this application. Catalase was also immobilized on oxirane acrylic beads, and the two separate catalysts used together, or both enzymes were co-immobilized on the same support, and this single catalyst added to the reaction mixture (the latter method being preferred).

Many of the deficiencies of the soluble enzymes were eliminated by employing the immobilized enzyme catalyst. The stability of immobilized glycolate oxidase in aqueous buffers is much greater than the soluble enzyme (approaching the stability of ammonium sulfate-precipitated enzyme). Recovery and reuse of the co-immobilized catalyst was easily performed by simply filtering the catalyst away from the reaction mixture and recycling it to fresh reaction mixture; in this manner for immobilized glycolate oxidase the number of turnovers (i.e., the number of substrate molecules that are converted to product molecules per catalyst molecule before inactivation of the enzyme) as high as $10^7$ (mol/mol) have been obtained. Finally, the ability to bubble oxygen through the reaction mixture without denaturing the enzyme catalyst resulted in increases in the reaction rate of at least ten-fold, and this increase in rate significantly reduces the cost of manufacture for this process.

The immobilized glycolate oxidase used in the reaction should be present in an effective concentration, usually a concentration of about 0.001 to about 10.0 IU/mL, preferably about 0.1 to about 4 IU/mL. An IU (International Unit) is defined as the amount of enzyme that will catalyze the transformation of one micromole of substrate per minute. A procedure for the assay of this enzyme is found in I. Zelitch and S. Ochoa, *J. Biol. Chem.*, Vol. 201, 707–718 (1953). This method is also used to assay the activity of recovered or recycled glycolate oxidase.

The pH of the reaction solution should be between 7 and 10, preferably between 8.0 and 9.5. The pH can be maintained by a buffer, since enzyme activity varies with pH. The pH of the reaction decreases slightly as the reaction proceeds, so it is often useful to start the reaction near the high end of the maximum enzyme activity pH range, about 9.0–9.5, and allow it to drop during the reaction. As has been previously described in U.S. Ser. No. 07/422,011, filed Oct. 16, 1989, an amine buffer capable of complexing the glyoxylic acid (by forming an imine which is more stable to chemical or enzymatic oxidation) is employed along with catalase to maximize product selectivity. Ethylenediamine, or less preferably, tris(hydroxymethyl)methylamine (hereinafter TRIS), piperazine, or glycylglycine improved the yield of glyoxylic acid. These amines are used in a molar ratio of amine/glycolic acid (starting amount) of 1.0 to 3.0, preferably 1.05 to 1.33. Within this range, the exact value may be adjusted to obtain the desired pH. With very basic amines used at high amine to glycolic acid ratios, it may be necessary to adjust the pH, as by adding acid, for example hydrochloric or sulfuric acids. With less basic amines such as TRIS, it may be necessary to add a base to maintain the desired pH.

The concentration of immobilized catalase should be 50 to 100,000 IU/mL, preferably 350 to 14,000 IU/mL. It is preferred that the enzymes be co-immobilized to limit the amount of catalyst added to the reaction, and that the catalase and glycolate oxidase concentrations be adjusted within the above ranges so that the ratio (measured in IU for each) of catalase:glycolate oxidase is at least about 250:1. Flavinmononucleotide (FMN) is an optional added ingredient, used at a concentration of 0.0 to 2.0 mM, preferably 0.01 to 0.2 mM.

The reaction rate is at least partially controlled by the rate at which oxygen can be dissolved into the aqueous medium. Oxygen can be added to the reaction as the oxygen in air, but it is preferred to use a relatively pure form of oxygen, and to use elevated pressures. Although no upper limit of oxygen pressure is known, oxygen pressures up to 50 atmospheres may be used, and an upper limit of 15 atmospheres is preferred. Sparging (bubbling) oxygen through the reaction mixture is necessary to maintain a high oxygen dissolution (and hence reaction) rate. Oxygen is sparged through the reaction mixture at a rate of 0.05 to 5 volumes of oxygen (measured at atmospheric pressure) per volume of reaction mixture per minute (vol/vol·min), and preferably between 0.2 and 2 vol/vol·min. Additionally, a convenient form of agitation is useful, such as stirring.

The reaction temperature is an important variable, in that it affects reaction rate and the stability of the enzymes. A reaction temperature of 0° C. to 40° C. may be used, but the preferred reaction temperature range is from 5° C. to 15° C. Operating in the preferred temperature range maximizes recovered enzyme activity at the end of the reaction.

Upon completion of the reaction and removal of the enzyme catalyst by filtration or centrifugation, the amine buffer is most conveniently removed by use of an ion exchange resin. Suitable acidic cationic exchange resins include "AMBERLITE" CG120 or "AMBERLITE" IR120 (Rohm & Haas Co.), and "DOWEX" 50 (Dow Chemical Co.). The amine may then be recovered and subsequently recycled by treatment of the resin with strong base.

The product, glyoxylic acid, is useful in the preparation of vanillin and ethylvanillin, as well as being used in ion exchange resins and as an acid catalyst in the pharmaceutical industry (Ullmanns). It is usually sold as a 50% (weight percent) aqueous solution. It is also to be understood that reference to glyoxylic acid in this application can also mean the glyoxylate anion, especially when the glyoxylic acid is present in a solution whose pH is greater than about 2.3.

Purification of Glycolate Oxidase from Spinach Leaves

Glycolate oxidase from spinach was purified using selective ammonium sulfate fractionation followed by batch adsorption of the extract using DEAE cellulose. The latter procedure resulted in the adsorption of virtually all plant proteins except glycolate oxidase. All steps in the purification were performed at 4° C. unless otherwise stated. At 25° C., two bushels (16 kg) of fresh spinach were chopped into fine particles using a Fitz Mill grinder fitted with a 0.5 inch mesh screen. The liquid fraction (ca. 6L) of the resulting pulp was isolated by squeezing through 4 layers of cheesecloth; alternatively, a juice extractor (Vitantonio) may be used. To the liquid fraction was added 5.6 g of dithiothreitol (5 mM final concentration), then the pH was adjusted to 5.2 by adding 5-20 mL of 20% acetic acid. After a 10 minute incubation, the resulting mixture was centrifuged at 13,000 g for 25 min. at 4° C. using a GS-3 rotor (Sorvall). The pellet was discarded, and the pH of the supernatant adjusted to 7.5-8.0 using 15-20 mL of 6N potassium hydroxide (Zelitch, I., Ochoa, S., *J. Biol. Chem.*, Vol. 201, 707 (1953); Frigerio, N. A., Harbury, H. A., *J. Biol. Chem.*, Vol. 231, 135 (1958)). The supernatant (approx. 5.5L) was then concentrated 5-fold using a Pelicon (Millipore) ultrafiltration apparatus fitted with a 100,000 MW membrane cassette; the final volume of concentrate was approx. 1.1L. To the concentrate was then added solid ammonium sulfate (154 g) slowly over 10 min. After all the ammonium sulfate dissolved, the resulting precipitate was removed by centrifuging for 25 min. at 13,000 g. The pellet was discarded, and 77 g of ammonium sulfate was added to the supernatant (approx. 1.1L), which was then centrifuged as before. The resulting protein pellet was collected and the supernatant discarded (Zelitch (1953); Frigerio (1958)).

The protein pellet was dissolved in approx. 200 mL of 20 mM bicine buffer (pH 8.0). Using Spectropor 2 dialysis tubing (12,000–14,000 MWCO), the protein was dialysed for 16 hrs. vs. 4L of 20 mM bicine (pH 8.0) containing 2 mM FMN. The conductivity of the protein solution was measured relative to the conductivity of fresh bicine buffer using a conductivity meter, and if the readings were not equivalent, the protein solution was dialysed an additional 4 hrs, then tested as before. The dialysed protein solution (approx. 250 ml) was stirred in a beaker using either a magnetic stir bar or overhead stirrer, then 25 g of pre-swollen DEAE cellulose (Sigma) (Kerr, M. W., Groves, D., *Phytochemistry*, Vol. 14, 359-362 (1975)) added and the resulting mixture incubated for 10 minutes. Protein binding to the resin was monitored by following the decrease in protein concentration of the solution using the Bradford assay (Bio-Rad). When the protein concentration of the supernatant was reduced to trace levels (0.2 mg/mL), the unbound protein was recovered from the mixture by vacuum filtration through a 11-cm Whatman #1 filter disk in a 13 cm diameter Buchner funnel (Cole-Parmer). To maximize enzyme recovery, the resin cake was washed with 100 mL of 20 mM bicine (pH 8.0). Flavin mononucleotide (FMN, Sigma) was added to the protein solution to a 2 mM final concentration, then 240 g of solid ammonium sulfate was added to the enzyme solution (approx. 400 mL) gradually over 15 minutes with stirring while maintaining the pH at 8.0 by the dropwise addition of 5N potassium hydroxide. The resulting precipitated glycolate oxidase was stored in the dark at 4° C. until needed.

Purification of Catalase from Fresh Bakers Yeast

All steps of the purification were performed at 4° C. Fresh Baker's yeast (1 lb., Universal Foods-Red Star), was suspended in 450 mL of 20 mM Tris buffer (pH 7.5) containing 1 mM phenylmethylsulfonyl-fluoride (PMSF, Sigma). A 200 mL portion of the yeast suspension was transferred to a 400 mL capacity Bead Beater blender containing 200 mL of glass beads (0.5 mm diameter-Biospec Products), and after 5 min. of continuous mixing, the lysate was transferred to a receiving vessel (on ice). The remaining yeast suspension was processed in the same manner.

Cell debris was removed by centrifuging the extract at 4° C. for 45 min.–1 hr. at 13,000 g in a GS-3 rotor (Sorvall). The supernatant (400 mL) was collected and 90.4 g of solid ammonium sulfate dissolved into the solution to achieve 40% saturation, then after incubation for 10 min. on ice the suspension was centrifuged at 4° C. for 25 min. at 13,000 g in a GSA rotor (Sorvall). The pellet was discarded, then 48 g of solid ammonium sulfate was added to the supernatant (400 mL) to achieve a final 60% saturation (Seah, T. C. M., Kaplan, J. G. J. Biol. Chem. Vol. 218, No. 8, 2880 (1973)). This mixture was incubated and centrifuged as before, and the resulting protein pellet was dissolved in a minimal volume of 20 mM TRIS (pH 7.5). Using Spectropor 2 dialysis tubing, the protein solution was dialysed against 20 mM TRIS (pH 7.5); the dialysis buffer was discarded and replenished after 16 hrs. The dialysis was continued for an additional 4 hrs., then the dialysed protein (100 mL) was recovered.

A 50-mL portion of the dialysed protein was loaded onto a radial flow chromatography column (Sepragen) packed with 100 mL of Q Sepharose fast flow ion exchange resin (Pharmacia), and the unbound protein eluted with 20 mM TRIS (pH 7.5) at 10 mL/min. Protein elution was monitored using a flow cell fitted with a 280 nm filter (LKB) linked to a chart recorder (LKB); 10–15 mL column fractions were collected using an LKB fraction collector. When all unbound protein had eluted from the column, a 400 mL linear gradient of NaCl from 0–500 mM dissolved in 20 mM TRIS (pH 7.5) was started at 10 mL/min., and fractions assayed for catalase activity by monitoring for the disappearance of peroxide at 240 nm. Fractions with catalase activity were pooled, and ammonium sulfate added to a final concentration of 80% saturation. The resulting precipitated catalase was stored at 4° C.

This purification method has also been used to purify catalase from *Aspergillus nidulans* and *Aspergillus niger*.

Enzyme Assays for Glycolate Oxidase and Catalase Immobilized on Oxirane Acrylic Beads Glycolate oxidase immobilized on oxirane acrylic beads was assayed by accurately weighing ca. 5–10 mg of the treated beads into a 3-mL quartz cuvette containing a magnetic stirring bar, then 2.0 mL of a solution which was 0.12 mM in 2,6-dichlorophenol-indophenol and 80 mM in TRIS buffer (pH 8.3) was added. The cuvette was capped with a rubber septum and the solution deoxygenated by bubbling with nitrogen for 5 min. To the cuvette was then added by syringe 40 μL of 1.0M glycolic acid/1.0M TRIS (pH 8.3), and the mixture stirred while measuring the change in adsorption with time at 605 nm (e=22,000).

Catalase activity was assayed by accurately weighing ca. 2–5 mg of the treated beads into a 3 mL quartz cuvette containing a magnetic stirring bar, then adding 2.0 mL of a distilled water, and 1.0 mL of 59 mM hydrogen peroxide in 50 mM phosphate buffer (pH 7.0) and measuring the change in absorption with time at 240 nm (e=39.4). Activities of immobilized glycolate oxidase and catalase were typically 6 IU/gram beads and 6000 IU/gram beads, respectively.

HPLC Analysis for Glycolic, Glyoxylic, Oxalic, and Formic Acid

Samples for analysis were prepared by mixing 0.100 mL of the reaction mixture with 0.300 mL of 0.1N $H_2SO_4$, then filtering the resulting solution through a Millipore Ultrafree MC filter unit (10,000 mw cutoff). Analyses for glycolic acid, glyoxylic acid, oxalic acid and formic acid were performed by high performance liquid chromatography (HPLC) on a Bio-Rad Aminex HPX-87H column (300×7.8 mm) at 40° C., using as solvent an aqueous solution of $H_2SO_4$(0.01N) and 1-hydroxyethane-1,1 -diphosphonic acid (0.1 mM) at 1.0 mL/minute. The instrument was a Waters 840 HPLC system with Model 510 pumps, a 712 WISP autosampler, and, in sequence, a 490E UV detector and 410 differential refractometer. UV analysis was performed at 210 nm. The retention times for oxalic acid, glyoxylic acid, glycolic acid, formic acid, and propionic acid (internal standard) were 4.29, 6.09, 7.77, 8.79, and 11.41 minutes, respectively.

Example 1

Immobilization of Glycolate Oxidase on Various Supports

Poly(ethyleneimine) (PEI), poly(ethyl-eneimine) on silica gel, benzylated poly(ethyl-eneimine) on silica gel, Bio-Rex 70, CH Sepharose 4B, XAD-4, XAD-8, Phenyl Agarose, Eupergit C, Eupergit C-250L, and Eupergit C-30N were all obtained from commercial sources. PAN-500 (Poly(acrylamide-co-N-acryloxysuccinimide)) gel crosslinked with triethylenetetramine) was prepared and used to immobilize glycolate oxidase according to the procedures described by Pollack, A., et al. J. Am. Chem. Soc., 1980, 102, 6324–6336. For those supports which bind protein by physical adsorption, immobilizations were performed by washing the support with an aqueous buffer at pH 5–10 as appropriate, then exposing the support to a buffered solution of the enzymes for a predetermined time at either 5° C. or 25° C., then washing the support with fresh buffer 3–4 times to remove any unadsorbed enzyme and assaying the support for glycolate oxidase activity. For supports used in conjunction with glutaraldehyde, the procedure outlined above was repeated except that prior to addition of the enzyme, the supports were treated with 5% aqueous glutaraldehyde. A detailed procedure for the immobilization of glycolate oxidase on Eupergit is given in Example 2. The yields of immobilized glycolate oxidase listed in the table below were obtained by optimizing the immobilization conditions for each support, and are based on the total amount of enzyme activity added during each procedure.

| SUPPORT | % YIELD | ACTIVITY | ATTACHMENT |
|---|---|---|---|
| PEI | 0 | 0 | ionic adsorption |
| PEI/glutaraldehyde | 0 | 0 | covalent |
| PEI-silica/glutar. | 0 | 0 | covalent |
| Bio-Rex 70 | 0 | 0 | ionic adsorption |
| CH Sepharose 4B | 0 | 0 | ionic adsorption |
| CNBr-Agarose | 20 | 5.0 IU/mL | covalent |
| PAN-500 gel | 19 | 0.14 IU/mL | covalent |
| XAD-4 | 0 | 0 | physical adsorpt. |
| XAD-8 | 4 | 0.76 IU/gr | physical adsorpt. |
| PEI-silica/benzyl. | 0 | 0 | physical adsorpt. |
| Phenyl Agarose | 3 | 0.62 IU/gr | physical adsorpt. |
| Eupergit C | 17 | 7.8 IU/gr | covalent |

| SUPPORT | % YIELD | ACTIVITY | ATTACHMENT |
|---|---|---|---|
| Eupergit C-250L | 8 | 5.0 IU/gr | covalent |

Example 2

Co-immobilization of Glycolate Oxidase and Catalase on Eupergit C

Into a 125-mL erlenmeyer flask was weighed 10.0 g of oxirane acrylic beads (Eupergit C). To the flask was then added ca. 75 mL of a solution containing 50 mM bicine buffer (pH 8.0) and 0.02 mM flavin mononucleotide, and the oxirane acrylic beads were then suspended in the buffer by swirling the contents of the flask. After the beads had settled to the bottom of the flask, the fines which floated to the top of the mixture were removed by pipet, along with as much of the supernatant which could be removed without disturbing the settled beads. This washing procedure was repeated a second time.

A 100-mL, ammonium sulfate-precipitated glycolate oxidase mixture, containing 327 IU of glycolate oxidase activity (isolated from fresh spinach leaves), was centrifuged at 12,000 rpm for 20 min (Sorvall GSA rotor at 4° C.). The supernatant was discarded and the pellet dissolved in 50 mL of 50 mM bicine (pH 8.0), 0.02 mM flavin mononucleotide buffer. A 10-mL mixture containing 100 mg (715,000 IU) of ammonium sulfate-precipitated *Aspergillus niger* catalase (Sigma C-3515) was centrifuged at 15,000 rpm for 10 minutes (Sorvall SS-34 rotor). The supernatant was discarded and the pellet dissolved in the buffer containing the glycolate oxidase. This enzyme solution was then added to the flask containing the washed oxirane acrylic beads, and the final volume adjusted to 125 mL with additional buffer. The resulting mixture was transferred to a 250-mL polypropylene bottle, which was capped and placed on a bottle roller at 4–5 rpm for 16 hours at 15° C. The mixture was then poured into a chromatography column equipped with a fritted bed support, allowed to drain, and the immobilized enzymes were washed three times with 30 mL of the bicine/FMN buffer and stored at 5° C. in this same buffer. The co-immobilized enzyme catalyst had 7.2 IU of glycolate oxidase activity/gram Eupergit C and 5680 IU of catalase activity/gram Eupergit C.

Example 3

Relative Stability of Soluble and Immobilized Glycolate Oxidase

The stability of unimmobilized (soluble) glycolate oxidase versus glycolate oxidase immobilized on oxirane acrylic beads (Eupergit C) was measured by storing either form of the enzyme at 4° C. in a buffered (pH 8.0) solution containing 2.0 mM flavin mononucleotide, then monitoring the enzyme activity with time. Additionally, the stability of the enzyme precipitated in 3.2M ammonium sulfate, 2.0 mM flavin mononucleotide, and stored under similar conditions was also monitored.

| Enzyme Recovery | 1 day | 2 days | 3 months | 6 months |
|---|---|---|---|---|
| soluble | 50% | 0 | 0 | 0 |
| immobilized | 92% | 95% | 50% | 50% |
| precipitated | 100% | 100% | 95% | 85% |

Example 4

Sparged Co-Immobilized Enzyme Reaction

Into a 2.5-cm ID×20 cm glass column equipped with a 20-μm polyethylene bed support was placed 10 mL of a solution containing glycolic acid (0.25M), ethylenediamine (0.33M), propionic acid (0.075M, HPLC internal standard), and flavin mononucleotide (0.2 mM). The column and its contents were cooled to 15° C., then 2.5 IU of spinach glycolate oxidase and 27,000 IU of *Aspergillus niger* catalase (co-immobilized on Eupergit C) were added to the solution. Oxygen was then passed through the porous bed support and bubbled through the reaction mixture at a rate of 10 mL/min. The reaction was monitored by taking a 100 μL aliquot of the reaction mixture at regular intervals, mixing the aliquot with 300 μL of 0.1N sulfuric acid to quench the reaction, filtering the aliquot and analyzing by HPLC. After 5.5 hours, the yields of glyoxylic acid, oxalic acid, and formic acid were 98%, 2%, and 0%, respectively, with complete conversion of glycolic acid. The final activities of glycolate oxidase and catalase were 95% and 65% of their initial values.

Comparative Example 1

Sparged Soluble Enzyme Reaction

The reaction described in Example 4 was repeated, except that the same amounts of soluble, unimmobilized glycolate oxidase and catalase were added to the reaction mixture. After 4 hours, the yields of glyoxylic acid, oxalic acid, and formic acid were 43%, 0%, and 0%, respectively, with a 46% conversion of glycolic acid. The final activities of glycolate oxidase and catalase were <2% and 82% of their initial values, respectively, and no further reaction was observed at longer reaction times.

Example 5

Sparged, Separately Immobilized Enzymes Reaction

The reaction in Example 4 was repeated using 10 mL of a solution containing glycolic acid (0.75M), ethylenediamine (0.86M), propionic acid (0.075M, HPLC internal standard), flavin mononucleotide (0.2 mM), 2.5 IU of spinach glycolate oxidase immobilized on Eupergit C, and 14,000 IU of *Aspergillus niger* catalase immobilized on Eupergit C (the two enzymes were not co-immobilized on the same support). After 20 hours, the yields of glyoxylic acid, oxalic acid, and formic acid were 99%, 0.2%, and 0.5%, respectively, with a 100% conversion of glycolic acid. The final activities of glycolate oxidase and catalase were 72% and 66% of their initial values, respectively.

Example 6

Fixed-bed Co-Immobilized Enzyme Reactor

Into a Kontes Airlift Bioreactor was placed 400 mL of a solution of 0.75M glycolic acid, 0.86M ethylenediamine, 0.075M propionic acid (HPLC internal standard), and 0.01 mM flavin mononucleotide (pH 9.0). Wet oxygen was bubbled through the solution in the bioreactor, and a peristaltic pump was used to recirculate the oxygenated solution (at 40 mL/min) from the bioreactor through a jacketed 1-cm ID×30-cm chromatography column containing spinach glycolate oxidase (13.9 IU) and *Aspergillus niger* catalase (56,000 IU) co-immobilized on Eupergit C oxirane acrylic beads (21-mL fixed bed volume). The contents of the bioreactor and jacketed chromatography column were maintained at 15° C. by recirculating 50:50 ethylene glycol/water through the jacket of the reactor and column using a refrigerated bath/circulator set at 10° C. After 377 hours, the yields of glyoxylic acid, oxalic acid, and formic acid were 93%, 0%, and 0.3%, respectively, with a 94% conversion of glycolic acid. The final activities of glycolate oxidase and catalase were 48% and 69% of their initial values.

Example 7

Oxidation of Glycolic Acid using Co-Immobilized Glycolate Oxidase/Catalase in a Stirred Autoclave Reactor A 300-mL EZE-Seal stirred autoclave (Autoclave Engineers) was charged with 100 mL of a solution containing glycolic acid (0.75M), ethylenediamine (0.86M, pH 9.0), propionic acid (0.075M, HPLC internal standard), and flavin mononucleotide (0.01 mM), and the solution cooled to 15° C. To the autoclave was then added 89 IU of spinach glycolate oxidase and 72,600 IU of *Aspergillus niger* catalase co-immobilized on ca. 28 g of Eupergit C. The resulting mixture was stirred at 500 rpm and 15° C. under 70 psig (483 kPa) of oxygen, while bubbling oxygen through the mixture at 100 mL/min. The reaction was monitored by taking a 100 μL aliquot of the reaction mixture at regular intervals, mixing the aliquot with 300 μL of 0.1N sulfuric acid to quench the reaction, filtering the aliquot and analyzing by HPLC. After 3 hours, the yields of glyoxylic acid, oxalic acid, and formic acid were 100%, 0%, and 0%, respectively, with complete conversion of glycolic acid. The final activities of glycolate oxidase and catalase were 100% and 100% of their initial values.

Example 8

Recovery and Reuse of Co-Immobilized Glycolate Oxidase/Catalase in a Stirred Autoclave Reactor The immobilized enzyme catalyst was recovered from the reaction described in Example 7 by filtering the reaction mixture through a 2.5-cm ID×20 cm glass column equipped with a 20-μm polyethylene bed support. The remaining liquid adsorbed on the catalyst was removed by briefly passing a stream of nitrogen through the column, then the catalyst was resuspended in 100 mL of a fresh 15° C. solution containing glycolic acid (0.75M), ethylenediamine (0.86M), propionic acid (0.075M HPLC internal standard), and flavin mononucleotide (0.01 mM). The 300-mL autoclave reactor was again charged with this reaction mixture, and the reaction repeated. This catalyst recovery procedure was performed for 10 consecutive batch reactions, and the reaction time, the recovery of glycolate oxidase (G.O.) and catalase activity, and yield of glyoxylic acid are listed in the table below.

| Run # | Time (hours) | G.O. (%) | catalase (%) | Glyoxylic acid (%) |
|---|---|---|---|---|
| 1 | 3 | 100 | 100 | 100 |
| 2 | 2 | 100 | 100 | 96 |
| 3 | 2 | 98 | 70 | 97 |
| 4 | 2 | 64 | 100 | 100 |
| 5 | 2 | 80 | 92 | 100 |
| 6 | 2 | 77 | 77 | 98 |
| 7 | 2.5 | 78 | 96 | 100 |
| 8 | 2.5 | 75 | 100 | 100 |
| 9 | 3 | 77 | 89 | 100 |
| 10 | 3 | 85 | 100 | 93 |

Example 9

Reaction Rates for Sparged Enzymatic Oxidations of Glycolic Acid in a Stirred Autoclave Reactor A 300-mL EZE-Seal stirred autoclave (Autoclave Engineers) was charged with 100 mL of a solution containing glycolic acid (0.75M), ethylenediamine (0.86M, pH 9.0), propionic acid (0.075M, HPLC internal standard), and flavin mononucleotide (0.01 mM), and the solution cooled to 15° C. To the autoclave was then added 41 IU of spinach glycolate oxidase and 42,800 IU of *Aspergillus niger* catalase co-immobilized on ca. 15 g of Eupergit C. The resulting mixture was stirred at 400 rpm and 15° C. under 35, 70, 105, or 140 psig (242, 483, 724 or 965 kPa) of oxygen, while bubbling oxygen through the mixture at 50 mL/min. The reaction was monitored by taking a 100 μL aliquot of the reaction mixture at regular intervals, mixing the aliquot with 300 μL of 0.1N sulfuric acid to quench the reaction, filtering the aliquot and analyzing by HPLC. The rates for reactions run under 35, 70, 105, or 140 psig (242, 483, 724 or 965 kPa) of oxygen were 0.48, 0.54, 0.53, and 0.57 mmol/min of glycolic acid, respectively.

Comparative Example 2

Reaction Rates for Non-Sparged Enzymatic Oxidations of Glycolic Acid in a Stirred Autoclave Reactor The reactions in Example 9 were repeated in a stirred autoclave reactor, except that no oxygen was bubbled through the reaction mixtures. The rates for reactions run under 35, 70, or 105 psig (242, 483, or 724 kPa) of oxygen were 0.032, 0.053, and 0.071 mmol/min of glycolic acid, respectively.

Example 10

Enzymatic oxidation of Glycolic Acid Using Permeabilized Bakers Yeast with Immobilized Glycolate Oxidase The procedures described in Examples 7 and 8 were repeated, except that 50 IU of spinach glycolate oxidase immobilized on ca. 15 g of Eupergit C, and 4.0 g of fresh *Saccharomyces cerevisiae* (Bakers yeast, Red Star brand, Universal Foods) which had been permeabilized with isopropanol and contained 100,000 IU of catalase activity, were used as catalyst. The reaction mixture was stirred at 400 rpm and 15° C. under 70 psig (483 kPa) of oxygen, while bubbling oxygen through the mixture at 20 mL/min. Six consecutive batch reactions were run, and the reaction time, the recovery of glycolate oxidase (G.O.) and catalase activity, and yield of glyoxylic acid are listed in the table below.

| Run # | Time (hours) | G.O. (%) | Catalase (%) | Glyoxylic Acid (%) |
|---|---|---|---|---|
| 1 | 2.5 | 81 | 62 | 100 |
| 2 | 3 | 97 | 30 | 100 |
| 3 | 3 | 73 | 54 | 100 |
| 4 | 3 | 51 | 53 | 96 |
| 5 | 4 | 49 | 57 | 98 |
| 6 | 6 | 24 | 45 | 97 |

Example 11

Dependence of the Rate of Glycolic Acid Oxidation on Oxygen Sparge Rate

The procedure described in Example 7 was repeated using 52 IU of spinach glycolate oxidase and 95,000 IU of *Aspergillus niger* catalase co-immobilized on ca. 18 g of Eupergit C. The reaction mixture was stirred at 500 rpm and 15° C. under 70 psig (483 kPa) of oxygen, while sparging oxygen through the mixture at 5–50 mL/min. The rates of glyolic acid oxidation at different oxygen sparge rates are listed in the table below.

| mL $O_2$/min | mmol $O_2$/min | mmol glycolic acid/min |
|---|---|---|
| 5 | 0.40 | 0.22 |
| 10 | 0.57 | 0.45 |
| 15 | 0.70 | 0.67 |
| 20 | 0.79 | 0.89 |
| 25 | 0.78 | 1.11 |
| 30 | 0.99 | 1.34 |
| 50 | 1.10 | 2.23 |

Example 12

Dependence of the Rate of Glycolic Acid Oxidation on Autoclave Stirring Rate

The procedure described in Example 7 was repeated using 50 IU of spinach glycolate oxidase and 47,000 IU of *Aspergillus niger* catalase co-immobilized on ca. 15 g of Eupergit C. The reaction mixture was stirred at 100–500 rpm and 15° C. under 70 psig (483 kPa) of oxygen, while sparging oxygen through the mixture at 20 mL/min. The rates of glycolic acid oxidation at different stirring rates is listed in the table below.

| rpm | mmol glycolic acid/min |
|---|---|
| 100 | 0.08 |
| 200 | 0.15 |
| 300 | 0.22 |
| 400 | 0.43 |
| 500 | 0.45 |

Example 13

Dependence of the Rate of Glycolic Acid Oxidation on Glycolate Oxidase Concentration The procedure described in Example 7 was repeated using 80, 60, 40, or 20 IU of spinach glycolate oxidase and 1,400,000, 1,000,000, 70,000, or 35,000 IU of *Aspergillus niger* catalase co-immobilized, respectively, on Eupergit C. The reaction mixture was stirred at 400 rpm and 15° C. under 70 psig of oxygen, while sparging oxygen through the mixture at 20 mL/min. The rates of glycolic acid oxidation obtained using different concentrations of glycolate oxidase is listed in the table below.

| Glycolate Oxidase (IU/mL) | mmol glycolic acid/min |
|---|---|
| 0.2 | 0.20 |
| 0.4 | 0.30 |
| 0.6 | 0.36 |
| 0.8 | 0.57 |

Having thus described and exemplified the invention with a certain degree of particularity, it should be appreciated that the following claims are not to be so limited but are to be afforded a scope commensurate with the wording of each element of the claim and equivalents thereof.

We claim:

1. A process for the production of glyoxylic acid comprising contacting, in aqueous solution at a temperature of 0° to 40° C. and at a pH of 7 to 10, glycolic acid with oxygen in the presence of (1) catalysts comprising glycolate oxidase and catalase immobilized on oxirane acrylic beads as insoluble supports, and (2) an amine buffer capable of forming a chemical adduct with glyoxylic acid wherein the initial concentration of glycolic acid is 200 mM to 2500 mM, where the initial mole ratio of amine to glycolic acid is within a range of 1.0 to 3.0 and thereafter recovering glyoxylic acid.

2. The process of claim 1 wherein glycolate oxidase and catalase are co-immobilized on the same oxirane acrylic bead.

3. The process of claim 1 wherein from 0.01 to 10.0 IU/mL of immobilized glycolate oxidase is present.

4. The process of claim 3 wherein from 50 to 100,000 IU/mL of immobilized catalase is present.

5. The process of claim 4 wherein the oxygen is at a pressure from 1 to 50 atmospheres.

6. The process of claim 5 wherein from about 0.1 to about 4 IU/mL immobilized glycolate oxidase is present.

7. The process of claim 6 wherein from 350 to 14,000 IU/mL immobilized catalase is present.

8. The process of claim 7 wherein the reaction is carried out at 5° to 15° C.

9. The process of claim 8 wherein the amine buffer is selected from the group consisting of ethylenediamine, tris(hydroxymethyl)methylamine, piperazine, glycylglycine, and mixtures thereof.

10. The process of claim 1 wherein the ratio of immobilized catalase to immobilized glycolate oxidase is at least 250:1.

11. The process of claim 1 wherein the initial concentration of added flavin mononucleotide is from 0 to 2.0 mM.

12. The process of claim 1 wherein the amine buffer is ethylenediamine.

13. The process of claim 1 wherein the amine buffer is tris(hydroxymethyl)methylamine.

14. The process of claim 1 wherein the amine buffer is piperazine.

15. The process of claim 1 wherein the amine buffer is glycylglycine.

* * * * *